US010584083B2

(12) United States Patent
Patil et al.

(10) Patent No.: US 10,584,083 B2
(45) Date of Patent: Mar. 10, 2020

(54) NEO-ALCOHOL COMPOUNDS, PROCESSES FOR MAKING SAME AND USE THEREOF

(71) Applicant: ExxonMobil Chemical Patents Inc., Baytown, TX (US)

(72) Inventors: Abhimanyu O. Patil, Westfield, NJ (US); Kyle G. Lewis, Houston, TX (US); Satish Bodige, Wayne, NJ (US)

(73) Assignee: ExxonMobile Chemical Patents Inc., Baytown, TX (US)

( * ) Notice: Subject to any disclaimer, the term of this patent is extended or adjusted under 35 U.S.C. 154(b) by 0 days.

(21) Appl. No.: 16/032,539

(22) Filed: Jul. 11, 2018

(65) Prior Publication Data
US 2019/0100481 A1  Apr. 4, 2019

Related U.S. Application Data

(60) Provisional application No. 62/565,501, filed on Sep. 29, 2017.

(51) Int. Cl.
C07C 29/00     (2006.01)
C07C 29/147    (2006.01)
C07C 31/125    (2006.01)

(52) U.S. Cl.
CPC .......... C07C 29/147 (2013.01); C07C 31/125 (2013.01)

(58) Field of Classification Search
CPC .................................................... C07C 29/147
See application file for complete search history.

(56) References Cited

U.S. PATENT DOCUMENTS

| 2,460,182 | A  | 1/1949  | Geigy |
| 3,059,007 | A  | 12/1962 | Vos et al. |
| 3,910,963 | A  | 10/1975 | Souma et al. |
| 4,126,585 | A  | 11/1978 | Conrad et al. |
| 4,332,738 | A  | 6/1982  | Benitez et al. |
| 4,658,078 | A  | 4/1987  | Slaugh et al. |
| 5,646,332 | A  | 7/1997  | Cusumano et al. |
| 6,239,318 | B1 | 5/2001  | Schuler et al. |
| 2011/0084243 | A1 | 4/2011  | Cranor et al. |
| 2014/0011086 | A1 | 1/2014  | Fujdala et al. |
| 2015/0284350 | A1 | 10/2015 | Aruleswaran et al. |
| 2017/0183596 | A1 | 6/2017  | Ng et al. |
| 2018/0119045 | A1 | 5/2018  | Patil et al. |

FOREIGN PATENT DOCUMENTS

| DE | 10 2013 009323 | 12/2014 |
| EP | 0629603        | 12/1994 |
| EP | 2474537        | 7/2012  |
| JP | H0782216       | 3/1995  |
| WO | 2005/049542    | 6/2005  |

OTHER PUBLICATIONS

Prasad et al., "Convenient Methods for the Reduction of Amides, Nitriles, Carboxylic Esters, Acids and Hydroboration of Alkenes Using NaBH4/12 System," Tetrahedron, 1992, vol. 48, No. 22, pp. 4623-4628.
Jirosova et al., "Sphinganine-Like Biogenesis of (E)-1-Nitropentadec-1-ene in Termite Solders of the Genus Prorhinotermes," Chembiochem—a European Journal of Chemical Biology, 2014, vol. 15, No. 4, pp. 533-536.
Luo et al., "Comparative study on aroma compounds in Chinese-type and Japanese-type soy sauces," XP-002781154 (2011).
Achonduh et al., "From alkenes to alcohols by cobalt-catalyzed hydroformylation-reduction," Tetrahedron, 2015, vol. 71, No. 8, pp. 1241-1246.
Cho et al., "Facile Reduction of Carboxylic Acids, Esters, Acid Chlorides, Amides and Nitriles to Alcohols or Amines Using NaBH4/BF3.Et20," Bulletin of the Korean Chemical Society, 2004, pp. 407-409.
Lebedev et al., "Synthesis of branched carboxylic acids with .alpha.-olefins and carbon monoxide in the presence of boron fluoride dehydrate," Neftepererabotka I Neftekhimiya, 1972, No. 8, pp. 7-11.
Polgar et al., "Long-Chain Acids Containing a Quaternary Carbon Atom, Part II," Journal of the American Chemical Society, 1943, pp. 615-619.
Delmau et al., "Combined Extraction of Cesium and Strontium from Alkaline Nitrate Solutions," Solvent Extraction and Ion Exchange, 2006, vol. 24, No. 2, pp. 197-217.
Rautenstrauch, "Potassium carboxylates by direct carbonylation of potassium alkoxides," Helvetica Chimica Acta, 1987, vol. 70, No. 3, pp. 593-599.
Newman, "alpha, alpha-Di-t-butyi-beta-propiolactone and Methyldi-t-butylacetic Acid from Di-t-butyiketene," The Journal of Organic Chemistry, 1968, pp. 2144-2145.
Asano et al., "Syntheses of branched-chain fatty acids contained in tubercle bacilli. VI. Phthioic acid. 4," Yakugaku Zasshi, 1945, vol. 65, No. 4A, pp. 15-17.
Churilova et al., "Telomerization of propylene with carboxylic acids," Izvestiya Akademii Nauk SSSR, Seriya Khimicheskaya, 1975, vol. 11, pp. 2497-2501.
Stallberg-Stenhagen, "Optically active higher aliphatic compounds. XI. The synthesis of (-31 )-2-rnethy1-2-ethyieicosanoic acid," Arkiv Foer Kemi, 1951, vol. 3, pp. 273-280.
Bondareva et al., "Synthesis and extracting properties of triacylated ethyleneamines," Russian Journal of Applied Chemistry, 2011, vol. 84, No. 11, pp. 1897-1902.
Eidus et al., "Carbonylation of pentene-1 and 3-methylbutene-1 by carbon monoxide in the presence of hydrates of boron trifluoride," Bulletin of the Academy of Sciences of the USSR Division of Chemical Science, 1970, pp. 1585-1587.
U.S. Appl. No. 15/988,683, filed May 24, 2018 Chen et al.
Sarnavskaya, et al., "Volatility and thermooxidation stability of synthetic ester oils," Khimiya I Tekhnologiya Topliv I Masel, 1975, vol. 10, pp. 49-52 (Abstract).

(Continued)

Primary Examiner — Sikarl A Witherspoon
(74) Attorney, Agent, or Firm — John R. Wright; Siwen Chen

(57) ABSTRACT

This disclosure relates to neo-alcohol compounds derivable from neo-acids, use of such neo-alcohol compounds, and processes for making neo-alcohol products.

19 Claims, No Drawings

(56) References Cited

OTHER PUBLICATIONS

Pincock et al., "Alkylation of Ethyl, lsobornyl, and Menthyl Esters of 2-Methyibutanoic Acid," Journal of Organic Chemistry, 1964, vol. 29, No. 10, pp. 299-2992.

Pirozhkov et al., "Synthesis of allyl esters of neo acids," Zhurnal Prikladnoi Khlmll, 1976, vol. 49, No. 7, pp. 1646-1648 (Abstract).

Shapovalov, et al., "Radiation-induced telomerization of ethylene with methyl propionate," Deposited Doc., Viniti, 1975, vol. 32, No. 8, pp. 1628-1675 (Abstract).

Ye et al., "Nickel-catalyzed directed sulfenylation of sp2 and sp3 C-H bonds," Chemical Communications, 2015, vol. 51, No. 37, pp. 7863-7866.

Prout et al., "Unsymemetrical Quaternary Carbon Compounds. III. The Preparation and Resolution of Trialkylacetic Acids," Journal of Organic Chemistry, 1960, vol. 25, No. 5, pp. 835-838.

U.S. Appl. No. 15/988,716, filed May 24, 2018 Patil et al.

Didomenico et al., "Compounds containing quaternary carbons, their use in medical devices, and methods," PCT Int. Appl., 2003.

Wagner-Jauregg et al., "Cycloalkyl aliphatic acids and their chemotherapeutic trial in leprosy and tuberculosis," Arb. Staatl. Inst. Exptl. Therap. U. Forsch.-Inst. Chemotherap. 1939, Frankfurt, No. 37, pp. 22-27, From: Chem. Zentr., 1939, II, pp. 459-460.

Mndzhoyan et al., "Derivatives of substituted acetic acids, XIX, Synthesis of .beta.-substituted phenylethyl esters of dialkylaminoacetic acids," Doklady Akademii Nauk Armyanskoi SSR, 1959, vol. 29, pp. 235-243.

Re et al., "Cyclization of 3-carboxy-3,6-dimethyl-1,5-heptadiene, a terpene acid with the skeleton of Artemisia ketone," Helvetica Chirnica Acta, 1958, vol. 41, pp. 1695-1709.

U.S. Appl. No. 62/565,536, filed Sep. 29, 2017 Patil et al.

Kanth et al., "Selective Reduction of Carboxylic Acids into Alcohols Using NaBH4 and I2," J. Org. Chem., 1991, vol. 56, pp. 5964-5965.

NEO-ALCOHOL COMPOUNDS, PROCESSES FOR MAKING SAME AND USE THEREOF

PRIORITY CLAIM

This application claims priority to and the benefit of U.S. 62/565,501, filed Sep. 29, 2017, the content of which is incorporated herein by reference in its entirety.

FIELD OF THE DISCLOSURE

This disclosure relates to alcohol compounds, use thereof, and processes for making them. In particular, this disclosure relates to neo-alcohol compounds, use of neo-alcohol compounds, and processes for making neo-alcohol products.

BACKGROUND OF THE DISCLOSURE

Branched aliphatic primary alcohols, especially those having long carbon chains, have found use in many applications such as surfactants, solvents, wetting agents, solubilizing agents, emulsifiers, or as an intermediates for making derivatives such as esters and ethers that can be used as surfactants, solvents, wetting agents, solubilizing agents, emulsifiers, and lubricant base stocks or additives.

A specific type of branched aliphatic alcohols are Guerbet alcohols, which are beta-branched primary alcohols having the following general structure:

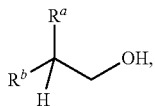

where $R^a$ and $R^b$ can be any hydrocarbyl group, preferably alkyl groups such as linear alkyl groups. Guerbet alcohol derivatives, such as esters, have found many use such as lubricant base stocks. Guerbet alcohols can be produced by Guerbet reaction, in which two primary alcohol molecules condense to produce a beta-branched primary alcohol molecule and water.

A neo-alcohol having general structure

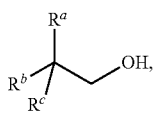

where $R^a$, $R^b$, and $R^c$ are independently hydrocarbyl groups, can have similar properties and uses of a Guerbet alcohol with similar molecular structure. Derivatives of neo-alcohols can find similar use to those of similar derivatives of Guerbet alcohols. Neo-alcohols and their derivatives can be particularly useful because of the presence of the quaternary carbon on the beta-location. Neo-alcohols comprising one or more long carbon chains having at least 6 carbons can be particularly interesting. Neo-alcohols cannot be made by Guerbet reaction.

Thus, there is a need for neo-alcohol products and a process for making such neo-alcohol products.

This disclosure satisfies this and other needs.

SUMMARY OF THE DISCLOSURE

It has been found that a class of neo-alcohols having a general formula

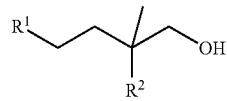

can be conveniently made by reducing a neo-acid having a general formula

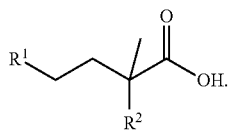

The neo-alcohols have interesting properties useful for a surfactant and can be used as such, and can be converted into useful derivatives.

A first aspect of this disclosure relates to a compound having the following formula (F-I):

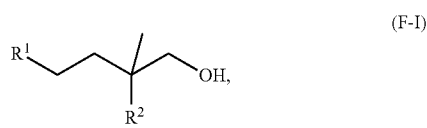

wherein $R^1$ and $R^2$ are independently each a hydrocarbyl group comprising at least two (2) carbon atoms (preferably a C2-C60 hydrocarbyl group).

A second aspect of this disclosure relates to use of the compound of the first aspect in in at least one of the following: (i) a lubricating oil composition as an additive component; (ii) a detergent composition as a surfactant; (iii) a pharmaceutical composition as a surfactant and/or solvent; (iv) a pesticide as a surfactant and/or solvent; (v) a herbicide as a surfactant and/or solvent; and (vi) a plastic material as a plasticizer.

A third aspect of this disclosure relates to a process for making a neo-alcohol product comprising a neo-alcohol compound having a formula (F-I) below:

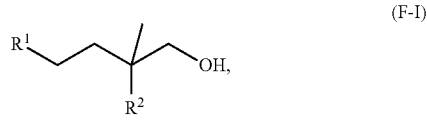

wherein $R^1$ and $R^2$ are independently each a hydrocarbyl group comprising at least two (2) carbon atoms (preferably a C2-C60 hydrocarbyl group, more preferably a C2-C30 linear or branched alkyl group), the process comprising: (I) providing a neo-acid product comprising a neo-acid compound having a formula (F-II) below:

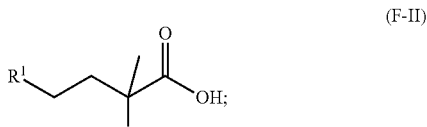

and (II) contacting the neo-acid product with a reducing agent under reducing conditions.

DETAILED DESCRIPTION OF THE DISCLOSURE

Definitions

In this disclosure, the indefinite article "a" or "an" means at least one, unless it is clearly specified or indicated by the context to mean one.

"Alkyl group" refers to a saturated hydrocarbyl group consisting of carbon and hydrogen atoms. "Linear alkyl group" refers to a non-cyclic alkyl group in which all carbon atoms are covalently connected to no more than two carbon atoms. "Branched alkyl group" refers to a non-cyclic alkyl group in which at least one carbon atom is covalently connected to more than two carbon atoms. "Cycloalkyl group" refers to an alkyl group in which all carbon atoms form a ring structure.

"Hydrocarbyl group" refers to a group consisting of hydrogen and carbon atoms only. A hydrocarbyl group can be saturated or unsaturated, linear or branched, cyclic or acyclic, containing a cyclic structure or free of cyclic structure, and aromatic or non-aromatic. A "substituted" hydrocarbyl group is a hydrocarbyl group in which a hydrogen atom is substituted with another group. An "unsubstituted" hydrocarbyl group is a hydrocarbyl group.

"Cn" group or compound refers to a group or a compound comprising carbon atoms at total number thereof of n. Thus, "Cm-Cn" or "Cm to Cn" group or compound refers to a group or compound comprising carbon atoms at a total number thereof in the range from m to n. Thus, a C1-C50 alkyl group refers to an alkyl group comprising carbon atoms at a total number thereof in the range from 1 to 50.

"Mono-ester" refers to a compound having one ester (—C(O)—O—) functional group therein.

"Neo-acid" refers to a carboxylic acid having the following general structure:

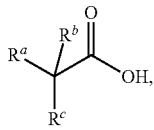

where $R^a$, $R^b$, and $R^c$, the same or different, are independently hydrocarbyl groups.

"Neo-alcohol" refers to an alcohol having the following general structure:

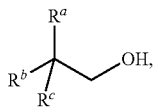

where $R^a$, $R^b$, and $R^c$, the same or different, are independently hydrocarbyl groups.

"Lubricating oil" refers to a substance that can be introduced between two or more surfaces and lowers the level of friction between two adjacent surfaces moving relative to each other. Non-limiting examples of lubricating oils include those in liquid form during normal use thereof such as engine oils and gear box oils, and those in viscous liquid form during normal use such as grease. A lubricating oil "base stock" is a material, typically a fluid at various levels of viscosity at the operating temperature of the lubricating oil, used to formulate a lubricating oil by admixing with other components. Non-limiting examples of base stocks suitable in lubricating oils include API Group I, Group II, Group III, Group IV, and Group V base stocks. If one base stock is designated as a primary base stock in the lubricating oil, any additional base stock may be called a co-base stock.

All kinematic viscosity values in this disclosure are as determined pursuant to ASTM D445. Kinematic viscosity at 100° C. is reported herein as KV100, and kinematic viscosity at 40° C. is reported herein as KV40. Unit of all KV100 and KV40 values herein is cSt unless otherwise specified.

All viscosity index ("VI") values in this disclosure are as determined pursuant to ASTM D2270.

All Noack volatility ("NV") values in this disclosure are as determined pursuant to ASTM D5800 unless specified otherwise. Unit of all NV values is wt %, unless otherwise specified.

All percentages in describing chemical compositions herein are by weight unless specified otherwise. "Wt %" means percent by weight.

"Consisting essentially of" means comprising at a concentration by weight of at least 90 wt %, based on the total weight of the mixture in question. Thus, a lubricating oil base stock consisting essentially of a given ester compound comprises that ester compound at a concentration by weight of at least 90 wt %, based on the total weight of the lubricating oil base stock.

All numerical values within the detailed description and the claims herein are modified by "about" or "approximately" the indicated value, taking into account experimental error and variations that would be expected by a person having ordinary skill in the art.

I. The Neo-Alcohol Compounds

One aspect of this disclosure is a novel category of alcohol compounds having a general formula (F-I) below:

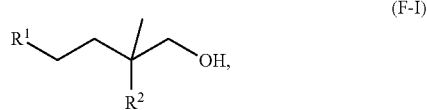

wherein $R^1$ and $R^2$ are independently each a hydrocarbyl group comprising at least two (2) carbon atoms (preferably a C2 to C60 hydrocarbyl group, more preferably a C2 to C60 alkyl group, still more preferably a C2 to C60 linear or branched alkyl group, still more preferably a C2 to C30 linear or branched alkyl group). A compound having molecular structure of (F-I) is a type of neo-alcohol, and is referred to as "neo-alcohol of this disclosure" herein.

In formula (F-I), preferably $R^1$ and $R^2$ each independently comprise c1 to c2 carbon atoms, where c1 and c2 can be, independently, any integer from 2 to 60, such as 2, 3, 4, 5, 6, 7, 8, 9, 10, 12, 14, 16, 18, 20, 22, 24, 26, 28, 30, 32, 34, 36, 38, 40, 42, 44, 46, 48, 50, 52, 54, 56, 58, or 60, as long as c1<c2. Preferably c1=2 and c2=30. More preferably c1=2 and c2=24. Still more preferably c1=4, and c2=16. Still more preferably c1=4, and c2=12. Preferably, $R^1$ and $R^2$ each independently comprise even number of carbon atoms.

At least one of $R^1$ and $R^2$ (preferably both $R^1$ and $R^2$ independently each) can be a branched alkyl group, preferably a branched alkyl group having the following formula (F-IV):

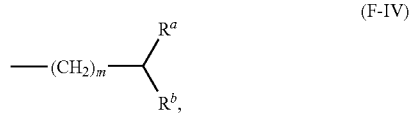

(F-IV)

where $R^a$ and $R^b$ are independently hydrocarbyl groups, preferably alkyl groups, more preferably linear or branched alkyl groups, still more preferably linear alkyl groups, m is a non-negative integer, preferably m≥2, more preferably m≥3, still more preferably m≥4, still more preferably m≥5, still more preferably m≥6, still more preferably m≥7. Preferably, $R^a$ and $R^b$ independently comprises c3 to c4 carbon atoms, where c3 and c4 can be, independently, any integer from 1 to 57, such as 1, 2, 3, 4, 5, 6, 7, 8, 9, 10, 12, 14, 16, 18, 20, 22, 23, 24, 26, 28, 30, 32, 34, 36, 38, 40, 42, 44, 46, 48, 50, 52, 54, 56, or 57, as long as c3<c4. More preferably c3=1 and c4=50. Still more preferably c3=1 and c4=40. Still more preferably c3=1 and c4=20. Still more preferably c3=1 and c4=16. Still more preferably c3=1, and c4=10. In one specific embodiment, m=0 and $R^1$ and/or $R^2$ can be a group branched at the 1-location, i.e., the carbon directly connected to the quaternary carbon atom. Non-limiting examples of branched alkyls for $R^1$ and $R^2$ include: 2-ethylhexyl, 2-propylheptanyl, 2-butyloctyl, and 3,5-dimethyloctyl.

At least one of $R^1$ and $R^2$ (preferably both $R^1$ and $R^2$ independently) can be linear alkyl groups such as: ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, n-pentacosyl, n-hexacosyl, n-octacosyl, and n-triacontyl. Preferably, the total number of carbon atoms in linear $R^1$ and $R^2$ is an even number. Preferably, the total number of carbon atoms in the linear $R^1$ and/or $R^2$ combined is from a1 to a2, where a1 and a2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as a1<a2. Preferably, the total number of carbon atoms in the linear $R^1$ and $R^2$ combined is from 8 to 96, more preferably from 8 to 80, more preferably from 8 to 64, still more preferably from 8 to 48, still more preferably from 8 to 40, still more preferably from 8 to 32, still more preferably from 8 to 28, still more preferably from 8 to 26, still more preferably from 8 to 24, still more preferably from 8 to 22, and still more preferably from 8 to 20.

Preferably, the total number of carbon atoms in $R^1$ and $R^2$ combined is from b1 to b2, where b1 and b2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as b1<b2. Preferably, the total number of carbon atoms in $R^1$ and $R^2$ is in a range from 8 to 96, more preferably from 8 to 80, still more preferably from 8 to 64, still more preferably from 8 to 48, still more preferably from 8 to 40, still more preferably from 8 to 32, still more preferably from 8 to 28, still more preferably from 8 to 26, still more preferably from 8 to 24, still more preferably from 8 to 22, and still more preferably from 8 to 20.

Preferably, $R^1$ and $R^2$ are identical. In such case, it is particularly preferred that $R^1$ and $R^2$ contain even number of carbon atoms. It is also particularly preferred that $R^1$ and $R^2$ are identical linear alkyl groups. Where $R^1$ and $R^2$ in formula (F-I) differ, it is highly desirable that they differ in terms of molar mass thereof by no greater than 145 (or 130, 115, 100, 85, 70, 55, 45, 30, or even 15) grams per mole. Preferably, in such cases, $R^1$ and $R^2$ differ in terms of total number of carbon atoms contained therein by no greater than 10 (or 9, 8, 7, 6, 5, 4, 3, 2, or even 1).

Particularly, desirable examples of the neo-alcohols of this disclosure are as follows: 2-ethyl-2-methylhexan-1-ol; 2-methyl-2-propylheptan-1-ol; 2-butyl-2-methyloctan-1-ol; 2-hexyl-2-methyldecan-1-ol; 2-methyl-2-octyldodecan-1-ol; 2-decyl-2-methyltetradecan-1-ol; 2-dodecyl-2-methylhexadecan-1-ol; 2-methyl-2-tetradecyloctadecan-1-ol; 2-hexadecyl-2-methylicosan-1-ol; 2-methyl-2-octadecyldocosan-1-ol; 2-icosyl-2-methyltetracosan-1-ol; 2-docosyl-2-methylhexacosan-1-ol; 2-methyl-2-tetracosyloctacosan-1-ol; and 2-hexacosyl-2-methyltriacontan-1-ol.

Among the above neo-alcohol compounds, the following are even more preferred: 2-ethyl-2-methylhexan-1-ol; 2-butyl-2-methyloctan-1-ol; 2-hexyl-2-methyldecan-1-ol; 2-methyl-2-octyldodecan-1-ol; 2-decyl-2-methyltetradecan-1-ol; and 2-dodecyl-2-methylhexadecan-1-ol.

II. Use of the Neo-Alcohol Compounds

Each molecule of neo-alcohols of this disclosure features a hydroxyl group that imparts polarity and hydrophilic properties. The hydrocarbon chains in the molecule, especially those relatively long chains having a carbon backbone comprising at least 6 carbon atoms, imparts hydrophobicity to the molecule at the end opposite to the hydroxyl group. The amphiphilic nature of the neo-alcohol molecule renders it suitable as a surfactant useful as detergents, wetting agents, emulsifiers, foaming agents, and dispersants.

Accordingly, the neo-alcohols of this disclosure can have many applications. One contemplated application is a lubricating oil composition (e.g., an additive package for a lubricating oil formulation; or a lubricating oil formulation). Other examples of applications include: detergents such as household laundry detergents and soaps; personal care products such as lotions, hair products, and the like; pharmaceutical products such as medicinal syrups; industrial products such as degreasers and industrial cleaners; pesticides; herbicides; and the like. The neo-alcohols of this disclosure can also be used as a plasticizer in plastic materials. Further, the neo-alcohols of this disclosure can be used in mining operations as a modifier of the formulation; as a compatibilizer in printing products such as ink formulations and toner formulations; and as a solvent or diluent in many chemical mixtures. All of these different products comprising neo-alcohol of this disclosure constitute individual aspects of this disclosure as well.

The neo-alcohols of this disclosure can be conveniently converted into many useful derivatives such as esters, ethers, and the like. Such derivatives can be conveniently used in many applications.

IIa. Lubricating Oil Compositions Containing Neo-Alcohol

In this disclosure, a lubricating oil formulation means a lubricating oil product ready for its intended use. Thus, examples of lubricating oil formulations include: engine oils ready for putting into the crankcase of an internal combustion engine; gear oils ready for being dispensed into a gear box; greases ready for being applied to apparatus in need of greasing; and the like. In this disclosure, a lubricating oil composition can be any portion or the entirety of a lubricating oil formulation. Thus, a lubricating oil composition can be: (i) a base stock; (ii) an additive package comprising one or more additives; (iii) a mixture of two or more base stocks absent any additive; (iv) a mixture of one or more base stocks with one or more additives but not the entirety of a lubricating oil formulation; and (v) a lubricating oil formulation in its entirety.

The neo-alcohols of this disclosure are useful as an additive component in formulating lubricating oil compositions. To make a final lubricating oil formulation as a product, one may add additional components, such as other base stocks, additional quantities of the materials already present in the lubricating oil composition, additive components, and the like, to the lubricating oil composition. A particularly preferred embodiment of the lubricating oil composition of this disclosure, however, is a lubricating oil formulation.

For example, the neo-alcohol can be present in a lubricating oil formulation as an additive component in an amount from about c1 to c2 wt %, based on the total weight of the oil composition, where c1 and c2 can be, independently, 0.01, 0.05, 0.1, 0.5, 1, 2, 3, 4, or 5, as long as c<c2.

Owing to the polarity of the neo-alcohols resulting from the hydroxyl group in their molecular structures, it has the ability to enhance sludge solvency and dispersancy and solvency and compared to other lubricating oil compositions free of alcohols.

IIa.1 Base Stocks Useful in the Lubricating Oil Compositions

A wide range of lubricating oil base stocks known in the art can be used in conjunction with the neo-alcohol in the lubricating oil compositions of this disclosure, as a primary base stock or a co-base stock. Such base stocks can be either derived from natural resources or synthetic, including un-refined, refined, or re-refined oils. Un-refined oil base stocks include shale oil obtained directly from retorting operations, petroleum oil obtained directly from primary distillation, and ester oil obtained directly from a natural source (such as plant matters and animal tissues) or directly from a chemical esterification process. Refined oil base stocks are those un-refined base stocks further subjected to one or more purification steps such as solvent extraction, secondary distillation, acid extraction, base extraction, filtration, and percolation to improve the at least one lubricating oil property. Re-refined oil base stocks are obtained by processes analogous to refined oils but using an oil that has been previously used as a feed stock.

API Groups I, II, III, IV, and V are broad categories of base stocks developed and defined by the American Petroleum Institute (API Publication 1509; www.API.org) to create guidelines for lubricating oil base stocks. Group I base stocks generally have a viscosity index of from about 80 to 120 and contain greater than about 0.03% sulfur and less than about 90% saturates. Group II base stocks generally have a viscosity index of from about 80 to 120, and contain less than or equal to about 0.03% sulfur and greater than or equal to about 90% saturates. Group III base stocks generally have a viscosity index greater than about 120 and contains less than or equal to about 0.03% sulfur and greater than about 90% saturates. Group IV includes polyalpha-olefins (PAO). Group V base stocks include base stocks not included in Groups I-IV. The table below summarizes properties of each of these five groups.

Natural oils include animal oils (e.g. lard), vegetable oils (e.g., castor oil), and mineral oils. Animal and vegetable oils possessing favorable thermal oxidation stability can be used. Of the natural oils, mineral oils are preferred. Mineral oils vary widely as to their crude source, e.g., as to whether they are paraffinic, naphthenic, or mixed paraffinic-naphthenic. Oils derived from coal or shale are also useful in this disclosure. Natural oils vary also as to the method used for their production and purification, e.g., their distillation range and whether they are straight run or cracked, hydrorefined, or solvent extracted.

Group II and/or Group III base stocks are generally hydroprocessed or hydrocracked base stocks derived from crude oil refining processes.

Synthetic base stocks include polymerized and interpolymerized olefins (e.g., polybutylenes, polypropylenes, propylene isobutylene copolymers, ethylene-olefin copolymers, and ethylene-alphaolefin copolymers).

Synthetic polyalpha-olefins ("PAO") base stocks are placed into Group IV. Advantageous Group IV base stocks are those made from one or more of C6, C8, C10, C12, and C14 linear alpha-olefins ("LAO"s). These base stocks can be commercially available at a wide range of viscosity, such as a KV100 in the range from 1.0 to 1,000 cSt. The PAO base stocks can be made by polymerization of the LAO(s) in the presence of Lewis-acid type catalyst or a metallocene compound-based catalyst system. High quality Group IV PAO commercial base stocks include the SpectraSyn™ and SpectraSyn Elite™ series available from ExxonMobil Chemical Company having an address at 4500 Bayway Drive, Baytown, Tex. 77520, United States.

All other synthetic base stocks, including but not limited to alkyl aromatics and synthetic esters are in Group V.

Additional esters not in the neo-acid-derived ester category in a minor amount may be useful in the lubricating oil compositions of this disclosure. Additive solvency and seal compatibility characteristics may be imparted by the use of esters such as the esters of dibasic acids with monoalkanols and the polyol esters of monocarboxylic acids. Esters of the former type include, e.g., the esters of dicarboxylic acids such as phthalic acid, succinic acid, sebacic acid, fumaric acid, adipic acid, linoleic acid dimer, malonic acid, alkyl malonic acid, alkenyl malonic acid, etc., with a variety of alcohols such as butyl alcohol, hexyl alcohol, dodecyl alcohol, 2-ethylhexyl alcohol, etc. Specific examples of these types of esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, etc. Useful ester-type Group V base stock include the Esterex™ series commercially available from ExxonMobil Chemical Company.

One or more of the following maybe used as a base stock in the lubricating oil of this disclosure as well: (1) one or more Gas-to-Liquids (GTL) materials; and (2) hydrodewaxed, hydroisomerized, solvent dewaxed, or catalytically dewaxed base stocks derived from synthetic wax, natural

| Base Stock Properties | | | |
|---|---|---|---|
| | Saturates | Sulfur | Viscosity Index |
| Group I | Higher than 90 and/or | Higher than 0.03% and | At least 80 and at most 120 |
| Group II | Higher than 90 and | At most 0.03% and | At least 80 and at most 120 |
| Group III | At least 90 and | At most 0.03% and | At least 120 |
| Group IV | | PAO products | |
| Group V | All other products not included in Groups I, II, III, and IV | | | wax, waxy feeds, slack waxes, gas oils, waxy fuels, hydrocracker bottoms, waxy raffinate, hydrocrackate, thermal crackates, foots oil, and waxy materials derived from coal liquefaction or shale oil. Such waxy feeds can be derived from mineral oils or non-mineral oil processing or can be synthetic (e.g., Fischer-Tropsch feed stocks). Such base stocks preferably comprise linear or branched hydrocarbyl compounds of C20 or higher, more preferably C30 or higher.

The lubricating oil compositions of this disclosure can comprise one or more Group I, II, III, IV, or V base stocks in addition to the neo-alcohol. Preferably, Group I base stocks, if any, are present at a relatively low concentration if a high quality lubricating oil is desired. Group I base stocks may be introduced as a diluent of an additive package at a small quantity. Groups II and III base stocks can be included in the lubricating oil compositions of this disclosure, but preferably only those with high quality, e.g., those having a VI from 100 to 120. Group IV and V base stocks, preferably those of high quality, are desirably included into the lubricating oil compositions of this disclosure.

IIa.2 Lubricating Oil Additives

The neo-alcohols of this disclosure can be advantageously used as an additive component in a lubricant oil composition. A lubricating oil composition containing a neo-acid of this disclosure may additionally contain one or more of other commonly used lubricating oil performance additives including but not limited to dispersants, detergents, viscosity modifiers, antiwear additives, corrosion inhibitors, rust inhibitors, metal deactivators, extreme pressure additives, anti-seizure agents, wax modifiers, viscosity modifiers, fluid-loss additives, seal compatibility agents, lubricity agents, anti-staining agents, chromophoric agents, defoamants, demulsifiers, densifiers, wetting agents, gelling agents, tackiness agents, colorants, and others. For a review of many commonly used additives and the quantities used, see: (i) Klamann in Lubricants and Related Products, Verlag Chemie, Deerfield Beach, Fla.; ISBN 0-89573-177-0; (ii) "Lubricant Additives," M. W. Ranney, published by Noyes Data Corporation of Parkridge, N J (1973); (iii) "Synthetics, Mineral Oils, and Bio-Based Lubricants," Edited by L. R. Rudnick, CRC Taylor and Francis, 2006, ISBN 1-57444-723-8; (iv) "Lubrication Fundamentals", J. G. Wills, Marcel Dekker Inc., (New York, 1980); (v) Synthetic Lubricants and High-Performance Functional Fluids, 2nd Ed., Rudnick and Shubkin, Marcel Dekker Inc., (New York, 1999); and (vi) "Polyalpha-olefins," L. R. Rudnick, Chemical Industries (Boca Raton, Fla., United States) (2006), 111 (Synthetics, Mineral Oils, and Bio-Based Lubricants), 3-36. Reference is also made to: (a) U.S. Pat. No. 7,704,930 B2; (b) U.S. Pat. No. 9,458,403 B2, Column 18, line 46 to Colum 39, line 68; (c) U.S. Pat. No. 9,422,497 B2, Column 34, line 4 to Colum 40, line 55; and (d) U.S. Pat. No. 8,048,833 B2, Column 17, line 48 to Colum 27, line 12, the disclosures of which are incorporated herein in their entirety. Additives, including the neo-alcohol(s) of this disclosure and other additives, are commonly delivered with varying amounts of diluent oil that may range from 5 wt % to 50 wt % based on the total weight of the additive package before incorporation into the formulated oil. The additives useful in this disclosure do not have to be soluble in the lubricating oil compositions. Insoluble additives in oil can be dispersed in the lubricating oil compositions of this disclosure. One or more of these other types of additive components may be combined with the neo-alcohol(s) of this disclosure and optional solvent/dispersing media (such as a Group I, II, III, IV, or V base stock) to form a mixture and delivered as an additive package. The additive package can be conveniently combined with other lubricating oil components, such as a primary base stock, one or more optional co-base stocks, and other additive packages, at desired quantities to make the final lubricating oil formulation (such as an engine oil) that can be directly used in its intended applications (such as in the crankcase of an internal combustion engine). As discussed above, an additive package for lubricating oil compositions is a special type of lubricating oil composition. It is noted that many of the additives are shipped from the additive manufacturer as a concentrate, containing one or more additives together, with a certain amount of base oil diluents. The neo-alcohol(s) of this disclosure as a lubricating additive and additive packages containing the neo-alcohols of this disclosure may be shipped as a concentrate as well, with a certain amount of base oil diluents.

When lubricating oil compositions contain one or more of the additives discussed above, the additive(s) are blended into the oil composition in an amount sufficient for it to perform its intended function.

IIb. Other Uses of the Neo-Alcohol of this Disclosure

The neo-alcohols of this disclosure, owing to the presence of a hydroxyl group and one or more hydrocarbon chain(s) in its molecule, exhibit amphiphilic properties, and thereby can be used as a surfactant in detergent compositions, pharmaceutical compositions, pesticide compositions, insecticide compositions, and herbicide compositions, to name a few. It can also function as a solvent in these compositions. The neo-alcohols of this disclosure can be conveniently converted into various derivatives, which can be used as surfactants in the above compositions as well.

Plasticizers are incorporated into a resin (usually a plastic or elastomer) to increase the flexibility, workability, or distensibility of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like. Other polymer systems that use small amounts of plasticizers include polyvinyl butyral, acrylic polymers, nylon, polyolefins, polyurethanes, and fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

There is increased interest in developing new plasticizers that offer good plasticizer performance characteristics (such as melting or chemical and thermal stability, pour point, glass transition, increased compatibility, good performance and low temperature properties) and are competitive economically.

The neo-alcohol of this disclosure can be advantageously used as a plasticizer described above.

The neo-alcohols of this disclosure can be advantageously used as an intermediate for making various chemical derivatives thereof. Such derivatives can include, but are not limited to, esters, ethers, polyethers (polyethylene oxide, polypropylene oxide, etc.) polyurethanes, sulfates, etc.

III. Method for Making the Neo-Alcohol Product

One aspect of this disclosure relates to a process for making a neo-alcohol product comprising a neo-alcohol compound having a formula (F-I) below:

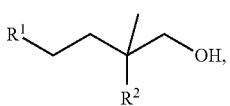

wherein $R^1$ and $R^2$ are each independently a hydrocarbyl group comprising at least two (2) carbon atoms (preferably a C2 to C60 hydrocarbyl group, more preferably a C2 to C60 alkyl group, still more preferably a C2 to C60 linear or branched alkyl group, and still more preferably a C2 to C30 linear or branched alkyl group), the process comprising: (I) providing a neo-acid product comprising a neo-acid compound having a formula (F-II):

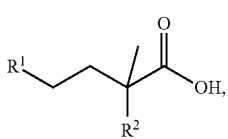

and (II) contacting the neo-acid product with a reducing agent under reducing conditions.

It is highly desirable that the neo-acid product used in the process consists essentially of a single mono-neo-acid, which will result in a neo-alcohol product consists essentially of a single neo-alcohol compound, though a mixture of multiple neo-acids having different formula (F-II) can be used as well, which will result in the production of a neo-alcohol product comprising multiple corresponding neo-alcohol compounds. The latter may be economically more advantageous where a mixture of different but similar neo-acids can be procured at a lower cost than a high-purity neo-acid compound, and a mixture of neo-alcohol derived from such neo-acid mixture is acceptable for the intended use thereof.

In formula (F-II), preferably $R^1$ and $R^2$ each independently comprise c1 to c2 carbon atoms, where c1 and c2 can be, independently, any integer from 2 to 60, such as 2, 3, 4, 5, 6, 7, 8, 9, 10, 12, 14, 16, 18, 20, 22, 24, 26, 28, 30, 32, 34, 36, 38, 40, 42, 44, 46, 48 50, 52, 54, 56, 58, or 60, as long as c1<c2. Preferably, c1=2 and c2=30. More preferably c1=2, and c2=24. Still more preferably c1=4, and c2=16. Preferably, $R^1$ and $R^2$ each independently comprise even number of carbon atoms.

At least one of $R^1$ and $R^2$ (preferably both $R^1$ and $R^2$ independently each) can be a branched alkyl group, preferably a branched alkyl group having the following formula (F-IV):

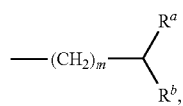

where $R^a$ and $R^b$ are independently hydrocarbyl groups, preferably alkyl groups, more preferably linear or branched alkyl groups, still more preferably linear alkyl groups, m is a non-negative integer, preferably m≥2, more preferably m≥3, still more preferably m≥4, still more preferably m≥5, still more preferably m≥6, still more preferably m≥7. Preferably, $R^a$ and $R^b$ independently comprises c3 to c4 carbon atoms, where c3 and c4 can be, independently, any integer from 1 to 57, such as 1, 2, 3, 4, 5, 6, 7, 8, 9, 10, 12, 14, 16, 18, 20, 22, 23, 24, 26, 28, 30, 32, 34, 36, 38, 40, 42, 44, 46, 48, 50, 52, 54, 56, or 57, as long as c3<c4. More preferably c3=1 and c4=50. Still more preferably c3=1 and c4=40. Still more preferably c3=1 and c4=20. Still more preferably c3=1 and c4=16. Still more preferably c3=1, and c4=10. In one specific embodiment, m=0 and $R^1$ and/or $R^2$ can be a group branched at the 1-location, i.e., the carbon directly connected to the quaternary carbon atom. Non-limiting examples of branched alkyls for $R^1$ and $R^2$ include: 2-ethylhexyl, 2-propylheptanyl, 2-butyloctyl, and 3,5-dimethyloctyl.

At least one of $R^1$ and $R^2$ (preferably, both $R^1$ and $R^2$ independently) can be linear alkyl groups such as: ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, n-pentacosyl, n-hexacosyl, n-octacosyl, and n-triacontyl. Preferably, the total number of carbon atoms in linear $R^1$ and $R^2$ is an even number. Preferably, the total number of carbon atoms in the linear $R^1$ and/or $R^2$ combined is from a1 to a2, where a1 and a2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as a1<a2. Preferably, the total number of carbon atoms in the linear $R^1$ and $R^2$ combined is from 8 to 96, more preferably from 8 to 80, still more preferably from 8 to 64, still more preferably from 8 to 48, still more preferably from 8 to 40, still more preferably from 8 to 32, still more preferably from 8 to 28, still more preferably from 8 to 26, still more preferably from 8 to 24, still more preferably from 8 to 22, and still more preferably from 8 to 20.

Preferably, the total number of carbon atoms in $R^1$ and $R^2$ combined is from b1 to b2, where b1 and b2 can be, independently, 8, 10, 12, 14, 16, 18, 20, 22, 24, 26, 28, 30, 32, 34, 36, 38, 40, 42, 44, 46, 48, 52, 56, 60, 64, 80, 96, or 100, as long as b1<b2. Preferably the total number of carbon atoms in $R^1$ and $R^2$ is in a range from 8 to 96, more preferably from 8 to 80, still more preferably from 8 to 64, still more preferably from 8 to 48, still more preferably from 8 to 40, still more preferably from 8 to 32, still more preferably from 8 to 28, still more preferably from 8 to 26, still more preferably from 8 to 24, still more preferably from 8 to 22, and still more preferably from 8 to 20.

Preferably, $R^1$ and $R^2$ are identical. In such case, it is particularly preferred that $R^1$ and $R^2$ contain even number of carbon atoms. It is also particularly preferred that $R^1$ and $R^2$ are identical linear alkyl groups. Where $R^1$ and $R^2$ differ, it is highly desirable that they differ in terms of molar mass thereof by no greater than 145 (or 130, 115, 100, 85, 70, 55, 45, 30, or even 15) grams per mole. Preferably, in such cases $R^1$ and $R^2$ differ in terms of total number of carbon atoms contained therein by no greater than 10 (or 9, 8, 7, 6, 5, 4, 3, 2, or even 1).

The neo-acid product useful in the process for making the neo-alcohols of this disclosure can be made from a process comprising the following steps: (Ia) providing a vinylidene olefin feed comprising a vinylidene olefin having the following formula (F-III):

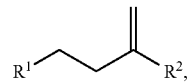

where $R^1$ and $R^2$ correspond to the $R^1$ and $R^2$ in formula (F-I); (Ib) contacting the vinylidene olefin with carbon monoxide in a reactor in the presence of an acid catalyst (preferably at a carbon monoxide partial pressure of at least 1.0 MPa, more preferably at least 3.5 MPa, still more preferably at least 5.0 MPa) to obtain a reaction mixture; (Ic) contacting the reaction mixture with water to obtain an acid product mixture; and (Id) obtaining at least a portion of the neo-acid product from the crude acid mixture.

The vinylidene olefin feed useful in step (Ia) above can be advantageously made from a terminal olefin monomer feed in a process comprising the following steps: (Ia.1) providing a monomer feed comprising a terminal olefin having a formula (F-IV) below and a terminal olefin having a formula (F-V) below: $R^1$—CH=$CH_2$ (F-IV); $R^2$—CH=$CH_2$ (F-V); where $R^1$ and $R^2$ correspond to the $R^1$ and $R^2$ in formulas (F-III), (F-II) and (F-I); (Ia.2) oligomerizing the monomer feed in an oligomerization reactor in the presence of a catalyst system comprising a metallocene compound to obtain an oligomerization product mixture; and (Ia.3) obtaining at least a portion of the vinylidene olefin feed from the oligomerization product mixture. In this process where $R^1$ and $R^2$ in formula (F-I) of the neo-alcohol are identical, a single terminal olefin having formula (F-IV) is used in the monomer feed. Where $R^1$ and $R^2$ in formula (F-I) of the neo-alcohol are different, at least two terminal olefin having different formulas (F-IV) are used in the monomer feed. In case two different terminal olefins are used in the monomer feed, the oligomerization product mixture obtainable from step (Ia.2) may comprise up to four vinylidene olefins as dimers of the two terminal olefins, which may be separated to obtain the desirable vinylidene olefin feed in step (Ia.3) comprising one, two, three, or all four vinylidene olefins, as the case may be. Nine vinylidene olefin dimers can result from three terminal olefins in the monomer feed. These different vinylidene olefins, if contained in the vinylidene olefin feed in step (Ia) of the process for making the neo-acid described above, can be converted into corresponding neo-acids in the neo-acid product, which, in turn, can be converted into corresponding neo-alcohols in the neo-alcohol product.

The above processes for making neo-acid product starting from terminal olefin monomer via the vinylidene olefin intermediate can be illustrated in the following Scheme-I:

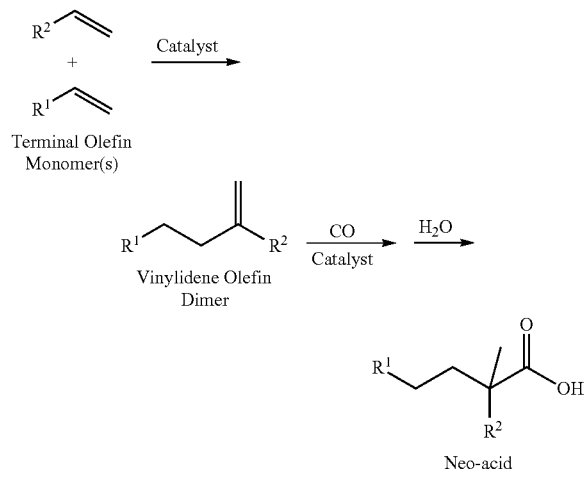

Only one type of vinylidene olefin dimer is illustrated in Scheme-I above. The processes are further described in greater detail below. Specific examples of Scheme-I is provided in Part A of the Examples in this disclosure.

IIIa. The Vinylidene Olefin Feed and Processes for Making them

The vinylidene olefin useful in the process of this disclosure for making the neo-acid product has a formula (F-III) below:

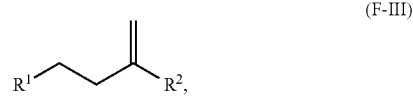

where $R^1$ and $R^2$ correspond to the $R^1$ and $R^2$ groups in formula (F-II) of the neo-acid, respectively, which, in turn, correspond to the $R^1$ and $R^2$ groups in formula (F-I) of the neo-alcohol, respectively.

Preferably, in the formula (F-III) of the vinylidene olefin, $R^1$ and $R^2$ are identical. Thus, examples of preferred vinylidene olefin having a formula (F-III) useful in the process of this disclosure are: 3-methyleneheptane; 4-methylenenonane; 5-methyleneundecane; 7-methyleneheptadecane; 9-methylenenonadecane; 11-methylenetricosane; 13-methyleneheptacosane; and 15-methylenehentriacontane, and mixtures thereof.

Where $R^1$ and $R^2$ in formula (F-III) differ, it is highly desirable that they differ in terms of molar mass thereof by no greater than 145 (or 130, 115, 100, 85, 70, 55, 45, 30, or even 15) grams per mole. In such cases, preferably, $R^1$ and $R^2$ differ in terms of total number of carbon atoms contained therein by no greater than 10 (or 9, 8, 7, 6, 5, 4, 3, 2, or even 1).

The vinylidene olefin having formula (F-III) can be advantageously made by dimerization of a monomer feed comprising a terminal olefin having a formula (F-III) and a terminal olefin having a formula (F-IV) below: $R^1$—CH=$CH_2$ (F-III); $R^2$—CH=$CH_2$ (F-IV), where $R^1$ and $R^2$ correspond to the $R^1$ and $R^2$ in (F-III), (F-II) and (F-I). It is highly desirable that the monomer feed consists essentially of a single terminal olefin having a formula (F-III). In such case, a single vinylidene olefin having a formula (F-III) where $R^1$ and $R^2$ are identical can be advantageously made in the dimerization process, which can be used as the vinylidene olefin feed in step (I) of the process of this disclosure for making a neo-acid product. It is contemplated that the monomer feed may comprise multiple terminal olefins having differing formulas (F-III). In such case, as discussed below, multiple vinylidene olefins having different formulas (F-III) may be produced in the dimerization reaction, which can be used together as the vinylidene olefin feed for making a neo-acid product comprising multiple neo-acid compounds. Where the monomer feed comprises multiple terminal olefins, it is highly desirable that they differ in terms of molecular weight thereof by no greater than 145 (or 130, 115, 100, 85, 70, 55, 45, 30, or even 15) grams per mole. In such cases, preferably, the multiple terminal olefins contained in the monomer feed differ in terms of total number of carbon atoms contained therein by no greater than 10 (or 9, 8, 7, 6, 5, 4, 3, 2, or even 1).

Such dimerization can be carried out advantageously in the presence of a catalyst system comprising a metallocene compound. U.S. Pat. No. 4,658,078 discloses a process for making a vinylidene olefin dimer from a terminal olefin monomer, the content of which is incorporated herein by reference in its entirety. The batch processes as disclosed in U.S. Pat. No. 4,658,078 resulted in the production of trimers and higher oligomers at various levels along with the intended dimer, which can be removed by, e.g., distillation, to obtain a substantially pure dimer product. The dimer product made in the batch processes of U.S. Pat. No. 4,658,078 may contain 1,2-di-substituted vinylene(s) and tri-substituted vinylenes at various levels. To the extent the concentrations of the 1,2-di-substituted vinylene(s) and tri-substituted vinylenes are acceptable to the intended application of this disclosure, the batch processes as disclosed in U.S. Pat. No. 4,658,078 may be used to produce the dimer having formula (F-III) above useful in the process for making the neo-acid product in this disclosure.

Such dimerization can also be carried out in the presence of trialkylaluminium such as tri(tert-butyl)aluminum as disclosed in U.S. Pat. No. 4,987,788, the content of which is incorporated by reference in its entirety.

Desirably, the vinylidene olefin having formula (F-III) feed used in the process of this disclosure for making neo-acid product comprises a single vinylidene olefin having formula (F-III) having a purity thereof of at least 90 wt %, preferably, at least 92 wt %, more preferably at least 94 wt %, still preferably at least 95 wt %, still more preferably 96 wt %, still more preferably at least 97 wt %, still more preferably at least 98 wt %, still more preferably at least 99 wt %, based on the total weight of the olefins contained in the feed.

It is possible to use a mixture of two or more vinylidene olefins having different formulae (F-III) as the vinylidene olefin feed in the process for making a mixture of neo-acid products as the neo-acid product. Desirably, the individual vinylidene olefins contained in the mixture have similar molecular weights, i.e., having molecular weights that differ by no more than, e.g., 145, 130, 115, 100, 85, 70, 55, 45, 30, or even 15 grams per mole. Desirably, the individual vinylidene olefins contained in the mixture differ in terms of total number of carbon atoms contained therein by no more than 10, 9, 8, 7, 6, 5, 4, 3, 2, or even 1. The individual vinylidene olefins contained in the mixture can be structural isomers. The vinylidene olefins having different chemical formulas and/or molecular weight can be converted into neo-acid compounds having different chemical formulas and/or molecular weight under the same reaction conditions following the same reaction mechanism. As long as the mixture of neo-acid compounds can be used for making a mixture neo-alcohol acceptable for the intended application, the corresponding mixture of vinylidene olefin can be used as the vinylidene olefin feed for making the neo-acid product by using the process of this disclosure.

It is highly desirable that the vinylidene olefin feed used in the process for making neo-acid product comprises 1,2-di-substituted vinylene(s) and tri-substituted vinylene(s) as impurities at a total concentration no greater than 5 wt %, preferably no greater than 4 wt %, still more preferably no greater than 3 wt %, still more preferably no greater than 2 wt %, still no greater than 1 wt %, based on the total weight of olefins contained in the feed.

Dimerization of the olefins $R^1$—CH=CH$_2$ and $R^2$—CH=CH$_2$ above can be effected in the presence of a catalyst system such as one comprising a metallocene compound. Co-pending, co-assigned U.S. Provisional Patent Application No. 62/551,081 (entitled "Process for Making Vinylidene Olefin" and having a filing date of Aug. 28, 2017) discloses vinylidene olefin dimers of terminal olefins useful for making neo-acids suitable for making neo-alcohols of this disclosure, and processes for making such vinylidene dimers, the content of which is incorporated herein by reference in its entirety.

IIIb. Carboxylation of the Vinvlidene Olefin to Make the Neo-Acid Compound

Koch chemistry can be employed to make neo-acids from the vinylidene olefins described above. The Koch chemistry involves a step (called "carboxylation" herein) of reacting the olefin with carbon monoxide in the presence of a strong acid at effective reaction temperature and an effective partial pressure of CO. Typically in a subsequent step, the reaction mixture from the carboxylation step of reacting with CO is allowed to contact with water to produce a carboxylic acid. It is highly desirable that the step of reacting the vinylidene olefin with CO is carried out in a batch reactor due to the pressurized nature. The reactions can be schematically illustrated as follows:

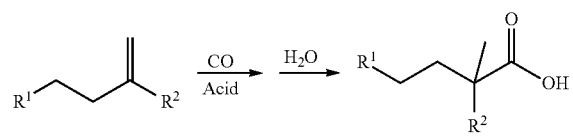

The acid catalyst used in the carboxylation step can be any strong organic or inorganic acids. Non-limiting examples are: (i) Brønsted acids such as HF; HCl; sulfuric acid; phosphorous acid; and mixtures thereof; (ii) solid acids such as activated clay; acid clay; faujasite; zeolites such as X-type zeolite, Y-type zeolite, and mordenite; oxides of transition metals such as zirconium, titanium, vanadium, tungsten, molybdenum, niobium, tantalum, and mixtures and compounds thereof; and combinations and mixtures thereof; (iii) acid resins; and (iv) Lewis acids such as $BF_3$, $AlCl_3$, and the like; and (v) any mixture and combination of any of categories (i), (ii), and (iii), such as HF and $BF_3$ mixture.

The amount of the acid catalyst used expressed in terms of molar ratio of the catalyst to the vinylidene olefin can range from r1 to r2, where $R^1$ and $R^2$ can be, independently, 0.01, 0.02, 0.04, 0.0.05, 0.06, 0.08, 0.1, 0.2, 0.4, 0.5, 0.6, 0.8, 1, 2, 4, 5, 6, 8, 10, 20, 40, or 50, as long as r1<r2. Preferably, r1=0.02 and r2=80. More preferably r1=0.05 and r2=50. Still more preferably, r1=0.1 and r2=10. Still more preferably r1=0.2 and r2=5. The quantity of the catalyst by mole means the quantity by mole of molecules, ions, or functional groups that provide the catalytic effect in the carboxylation reaction between the vinylidene olefin and CO in the catalyst material. Thus, the quantity by mole of a $BF_3$ catalyst means the quantity by mole of $BF_3 \cdot 1.1H_2O$. $BF_3 \cdot 2H_2O$ is believed to be not catalytically effective for the reaction between the vinylidene olefin and CO. However, subsequent addition of anhydrous $BF_3$ into the reaction system can convert $BF_3 \cdot 2H_2O$ into catalytically active form $BF_3 \cdot 1.1H_2O$. Thus in this disclosure, where $BF_3 \cdot 2H_2O$ and anhydrous $BF_3$ are introduced into the reaction system separately at stoichiometric quantities to form $BF_3 \cdot 1.1H_2O$, it is assumed that all $BF_3$ is present in the reaction system in the form of $BF_3 \cdot 1.1H_2O$ for the purpose of calculating the molar quantity of the $BF_3$ catalyst. The quantity of a HF catalyst by mole means the quantity by mole of protons provided by the catalyst (considered as equal to the quantity of HF because of the strong acidity of HF). For solid-phase catalyst materials such as the zeolites, solid acids and acidic resins, the quantity by mole means the quantity by mole of the functional groups or ions provided by the catalyst material.

Because the vinylidene olefin(s) can undergo oligomerization in the presence of the acid catalyst, in addition to the reaction pursuant to Koch chemistry, it is highly desirable that the active acid catalyst is not allowed to contact the olefin until after the olefin has already formed a mixture with CO at a high CO partial pressure in the reaction mixture. Thus, it is desirable that the active acid catalyst is added to the reaction system only after the partial pressure of CO in the reaction system has reached 2.0 mega Pascal ("MPa"), preferably 2.5 MPa, more preferably 3.0 MPa, still more preferably 3.5 kPa, still more preferably 5.0 MPa, still more preferably 7.0 MPa.

When $BF_3$ is used as an acid catalyst for the reaction between the vinylidene olefin and CO, it is highly desirable that a quantity of $BF_3.2H_2O$ is admixed with the vinylidene olefin feed in the reactor before CO partial pressure inside the reactor is increased to 2.0 MPa. Without intending to be bound by a particular theory, it is believed that the $BF_3.2H_2O$ is not catalytically effective for the oligomerization of the vinylidene olefin or the carboxylation reaction between the vinylidene olefin and CO. As such, to catalyze the carboxylation reaction, it is desired that after the CO partial pressure has reached a certain level as mentioned above, anhydrous $BF_3$ is introduced into the reactor to effect the carboxylation reaction between the vinylidene olefin and CO. Preferably the quantities of $BF_3.2H_2O$ and anhydrous $BF_3$ are at a substantially stoichiometric ratio to form $BF_3.1.1H_2O$.

Likewise, if a Brønsted acid such as $H_2SO_4$, HF, or $H_3PO_4$ is used as the acid catalyst, it is highly desired that the acid is not introduced into the reactor until the partial pressure of CO in the reactor has reached a certain level as discussed above.

In the event a solid acid is used as the catalyst in the carboxylation reaction, it is highly desired that the solid acid catalyst is distributed in an inert dispersant and introduced into the reactor only after the partial pressure of CO inside the reactor has reached a certain level as discussed above.

In the event it is desired to elevate the temperature of the reaction medium in the reactor to a higher level in order to achieve a desired conversion and/or reaction rate, it is highly desirable that CO partial pressure inside the reactor has reactor has reached a certain level as discussed above as well. Preferably, the temperature elevation process starts after at least a portion of the active catalyst is introduced into the reactor.

The catalyst can be added to the carboxylation reaction system as a solution in an inert solvent, as a substantially pure material, or as a dispersion in an inert dispersant. Non-limiting examples of the inert solvent and/or dispersant include: benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

The carboxylation reaction of the vinylidene olefin with CO is desirably conducted in the presence of an atmosphere comprising CO at an absolute partial pressure of CO in a range from p1 to p2 MPa, where p1 and p2 can be, independently, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, or 14.0, as long as p1<p2. A high total partial pressure of CO is conducive to a high conversion of the vinylidene. Desirably, the conversion of vinylidene in the carboxylation reaction is at least 70%, preferably at least 75%, more preferably at least 80%, more preferably at least 85%, more preferably at least 90%, still more preferably at least 95%.

The carboxylation reaction of the vinylidene olefin with CO is desirably conducted at a temperature in a range from t1° C. to t2° C., where t1 and t2 can be, independently, −20, −15, −10, −5, 0, 5, 10, 15, 20, 25, 30, 35, 40, 45, 50, 55, 60, 65, 70, 75, 80, 85, 90, 95, 100, 110, or 120, as long as t1<t2. Preferably, t1=0 and t2=100. More preferably, t1=25 and t2=80. A higher temperature is conductive to a higher conversion and a higher reaction rate, but at the expense of selectivity toward the desired neo-acid derived from the vinylidene olefin. Reaction time can range from 0.5 hour to 96 hours, preferably 1 hour to 60 hours, more preferably no longer than 48 hours, still more preferably no longer than 36 hours, still more preferably no longer than 24 hours, still more preferably no longer than 12 hours, still more preferably no longer than 6 hours.

Given the pressurized reaction condition, it is highly desired that the carboxylation between the vinylidene olefin and CO is conducted in a batch reactor that can withstand a high internal pressure. At the end of the reaction, the reactor is cooled down and depressurized, and the carboxylation product mixture, comprising unreacted vinylidene olefin, catalyst, the desired neo-acid product, and other undesired by-products, can be advantageously separated to obtain the neo-acid product.

The carboxylation reaction between the vinylidene olefin and CO may be conducted with or without the presence of an inert solvent. Non-limiting examples of the inert solvent include: benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

In the step of reacting the vinylidene olefin with CO in the presence of the acid catalyst, water may be included in the reactants at a small quantity, to the extent the presence of water does not reduce the activity of the catalyst. Upon completion of reaction with CO, the reaction mixture is typically allowed to contact with water to complete the carboxylation of the vinylidene olefin to produce the desired neo-acid product. The contact with water can result in the formation of a mixture including an aqueous phase and an organic phase. The acid is typically preferentially distributed in the organic phase, and any acid catalyst soluble in water or reactive with water can be preferentially distributed in the aqueous phase. Where a solid catalyst is utilized, such as solid zeolites, solid acids, and acid resin, the catalyst can be conveniently filtered from the liquid, dried and reused as appropriate in the carboxylation reaction. The neo-acid product in the organic phase may be further purified to obtain a neo-acid product comprising primarily the intended acid having a formula (F-II) with desired purity. Purification can be done via one or more of traditional methods such as water washing, solvent extraction, distillation, liquid or gas chromatography, or by using a sorbent.

In the process of making neo-acid product from vinylidene olefins, a high selectivity of the vinylidene olefin toward the desired neo-acid can be achieved in the carboxylation process if the active catalyst is not added to the reaction until a high CO partial pressure (e.g., a partial pressure of at least 5.0, 5.5, 6.0, 6.5, or 7.0 MPa) in the reaction system has been established, resulting in a neo-acid product having a purity of the desired neo-acid after removal of the vinylidene and heavy components of at least 95 wt %, 96 wt %, at least 97 wt %, at least 98 wt %, or even at least 99 wt %, based on the total weight of the neo-acid product. Such high purity of neo-acid is very surprising.

The combination of the carboxylation process with a continuous process for making high-purity vinylidene dimer of a terminal olefin monomer (the process described in co-pending, co-assigned U.S. Provisional Patent Application No. 62/551,081, entitled "Process for Making Vinylidene Olefin" and having a filing date of Aug. 28, 2017, the content of which is incorporated herein by reference in its entirety) as the vinylidene olefin used in the carboxylation process can result in a high conversion, high selectivity process for making the desired neo-acid from a terminal olefin feed and a CO feed.

Commercially available terminal olefins useful in the process of this disclosure include but are not limited to: 1-butene, 1-pentene, 1-hexene, 1-octene, 1-decene, 1-dodecene, 1-tetradecene, 1-hexadecene, 1-octadecene, 1-icosene, and the like. They can be conveniently used to fabricate neo-acids 2-ethyl-2-methylhexanoic acid, 2-methyl-2-propylheptanoic acid, 2-butyl-2-methyloctanoic acid, 2-hexyl-2-methyldecanoic acid, 2-methyl-2-octyldodecanoic acid, 2-decyl-2-methyltetradecanoic acid, 2-dodecyl-2-methylhexadecanoic acid, 2-methyl-2-tetradecyloctadecanoic acid, 2-hexadecyl-2-methylicosanoic acid, and 2-methyl-2-octadecyldocosanoic acid, respectively.

Non-limiting examples of neo-acids obtainable by the process described above and useful in the process of this disclosure for making neo-alcohol products include the following: 2-ethyl-2-methylhexanoic acid; 2-methyl-2-propylheptanoic acid; 2-butyl-2-methyloctanoic acid; 2-methyl-2-pentylnonanoic acid; 2-hexyl-2-methyldecanoic acid; 2-heptyl-2-methylundecanoic acid; 2-methyl-2-octyldodecanoic acid; 2-decyl-2-methyltetradecanoic acid; 2-dodecyl-2-methylhexadecanoic acid; 2-methyl-2-tetradecyloctadecanoic acid; and 2-methyl-2-hexadecylicosanoic acid.

Co-pending, co-assigned U.S. Provisional Patent Application Ser. No. 62/565,560, entitled "Neo-Acids and Process for Making the Same" and having a filing date of Sep. 29, 2017 discloses neo-acids suitable for use in the process of this disclosure for making neo-alcohols and processes for making neo-acids, the content of which is incorporated herein by reference in its entirety.

IIIc. Reduction of the Neo-Acid Product to Make the Neo-Alcohol Product

Reduction of the neo-acid having a formula (F-II) yields the neo-alcohol of this disclosure having a formula (F-I). Reduction of a carboxylic acid can be effected in many known ways by contacting the acid with a reducing agent under reducing conditions. Among them, mention can be made of hydrogenation in the presence of a hydrogenation catalyst, or contacting with other reducing agents in a solution or dispersion.

Hydrogenation of the neo-acid can be desirably effected by contacting the neo-acid with hydrogen atmosphere in the presence of a hydrogenation catalyst comprising a hydrogenation metal. The hydrogen atmosphere can have an absolute hydrogen partial pressure in a range from, e.g., p1 to p2 mega Pascal ("MPa"), where p1 and p2 can be, independently, 0.1, 0.2, 0.3, 0.4, 0.5, 0.6, 0.7, 0.8, 0.9, 1.0, 2.0, 4.0, 5.0, 6.0, 8.0, 10, 15, 20, 25, 30, 35, 40, 45, 50, 60, 70, 80, 90, 100, 200, 300, 400, 500, 600, 700, 800, 900, or even 1,000, as long as p1<p2. Preferably p2≤100. More preferably p2≤10. The hydrogenation metal can be selected from Fe, Co, Ni, Ru, Rh, Pd, Os, Ir, Pt, and combinations thereof. The hydrogenation metal may be supported on an inorganic support such as silica, alumina, and the like. One having ordinary skill in the art can choose the proper reaction temperature to effect the reduction of the neo-acid to neo-alcohol with desired conversion of the neo-acid and the desired selectivity toward the neo-alcohol.

Other typical reducing agents that may be used to convert the neo-acid to neo-alcohol of this disclosure include, but are not limited to: sodium borohydride ($NaBH_4$); lithium aluminum hydride; dithionate; thiosulfates; hydrazine; a mixture of $NaBH_4$ and iodine; a mixture of $NaBH_4$ and $H_2SO_4$; a mixture of $NaBH_4$, catechol, and $CF_3COOH$; a mixture of $NaBH_4$ and $ZnCl_2$; and a mixture of $NaBH_4$ and cyanuric chloride. Stoichiometric quantity of the reducing agent can be used to convert substantially all of the neo-acid into neo-alcohol. Desirably the reducing conditions are relatively mild, such as a temperature in the range from 0 to 100° C., preferably 0 to 80° C., more preferably 10 to 60° C., and still more preferably 20 to 50° C., and a reaction time in the range from 0.5 to 24 hours, preferably in the range from 0.5 to 20 hours, more preferably from 0.5 to 18 hours, more preferably from 0.5 to 15 hours, still more preferably from 1 to 12 hours, still more preferably from 1 to 6 hours.

The reduction reaction of the neo-acid can be conducted with or without the presence of an inert solvent. Non-limiting examples of the inert solvent include: benzene, toluene, any xylene, ethylbenzene, and mixtures thereof; n-pentane and branched isomers thereof, and mixtures thereof; n-hexane and branched isomers thereof, and mixtures thereof; cyclohexane and saturated isomers thereof, and mixtures thereof; n-heptane and branched isomers thereof, and mixtures thereof; n-octane and branched isomers thereof, and mixtures thereof; n-nonane and branched isomers thereof, and mixtures thereof; n-decane and branched isomers thereof, and mixtures thereof; and any mixture of the above; Isopar® solvent; and the like.

The reaction mixture resulting from the reduction reaction can comprise, among others, unreacted residual neo-acid, the desired neo-alcohol compound, catalyst if used, and the inert solvent if used. Known methods such as filtration, solvent extraction, distillation, chromatography, using sorbents, and the like, can be employed to obtain a neo-alcohol product comprising one or more neo-alcohol compounds of this disclosure at desirable purity thereof. For example, filtration can be used to separate solid materials such as hydrogenation catalyst particles from liquid. Solid catalyst thus separated can be regenerated and recycled. Washing with alkaline aqueous solutions such as water solutions of $NaCO_3$, $NaHCO_3$, and NaOH, and the like, can result in the conversion of organic metal salts (such as $NaBH_4$) and the residual neo-acid into water-soluble salts, and their distribution in an aqueous phase and the distribution of neo-alcohol in an organic phase when two immiscible phases (aqueous/organic phases) are present in and extraction mixture. Removal of organic solvent from the organic phase can result in a crude neo-alcohol product. The crude neo-alcohol product can be further purified by distillation, washing, extraction, sorbents, and the like, to obtain a neo-alcohol product comprising one or more neo-alcohol compounds of this disclosure with desired purity. Desirably, the neo-alcohol product consists essentially of neo-alcohol compound(s) of this disclosure. Preferably, the neo-alcohol product comprises neo-alcohol compound(s) of this disclosure at a concentration, based on the total weight of the neo-alcohol product, of at least 95 wt %, more preferably at least 96 wt %, still more preferably at least 97 wt %, still more preferably at least 98 wt %, still more preferably at least 99 wt %. Preferably, the neo-alcohol product consists essentially of a single neo-alcohol of this disclosure. More preferably, the neo-alcohol product comprises a single neo-alcohol compound of this disclosure at a concentration, based on the total weight of the neo-alcohol product, of at least 95 wt %, more preferably at least 96 wt %, still more preferably at least 97 wt %, still more preferably at least 98 wt %, still more preferably at least 99 wt %.

The neo-alcohol product made from the process of this disclosure can be desirably used for various applications. One contemplated application is as an additive component in a lubricating oil composition. Other examples of applications include: detergents such as household laundry detergents and soaps; personal care products such as lotions, hair care products, and the like; pharmaceutical products such as medicinal syrups; industrial products such as degreasers and industrial cleaners; pesticides; herbicides; and the like. The neo-alcohol product made from the process of this disclosure can also be used as a plasticizer in plastic materials.

Examples of techniques that can be employed to characterize the neo-alcohol described above include, but are not limited to, analytical gas chromatography, nuclear magnetic resonance, thermogravimetric analysis (TGA), inductively coupled plasma mass spectrometry, differential scanning calorimetry (DSC), and volatility and viscosity measurements.

This disclosure is further illustrated by the following non-limiting examples.

EXAMPLES

In the following examples, kinematic viscosity at 100° C. ("KV100") and 40° C. ("KV40") of fluids were determined pursuant to ASTM standards D-445; viscosity index ("VI") was determined pursuant to ASTM standard D-2270; and Noack volatility ("NV") were determined using thermal gravimetric analysis ("TGA").

Part A: Synthesis of 2-Methyl-2-octyldodecanoic Acid

Example A1: Synthesis of 9-methylenenonadecane

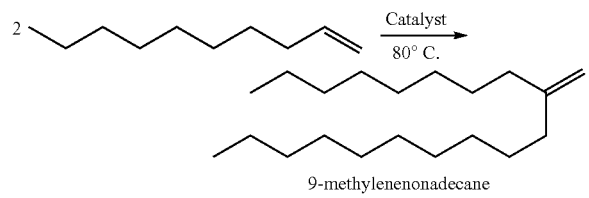

Into a batch reactor was charged 5000 grams of 1-decene (98.6% 1-decene, 0.7% 1-octene, 0.7% 1-dodecene), into which 50 grams of 10% MAO solution was added and held for 60 minutes at 80° C. 450 grams of catalyst solution (1.4 wt % biscyclopentadienyl zirconium (IV) dichloride dissolved in toluene) was subsequently added over 52 minutes. The reactor was held at 80° C. for 6 hours before the reaction was cooled and quenched with 10 ml of water. Gas chromatography showed reactor conversion was 74% with 88% selectivity to dimer and 12% selectivity to trimer and heavier species.

Filter aid was added thereafter into the fluid, which was filtered to remove Zr and/or Al-containing solid particles. The resultant mixture was then flashed to remove the residual monomer and distilled to remove heavies product to isolate the dimer species. The recovered dimer product was measured to contain dimers of the starting olefin at a concentration of 99.5 wt % by GC and a concentration of 9-methylenenonadecane at 98 mol % (by $^1$H NMR).

Example A2: Synthesis of 2-Methyl-2-octyldodecanoic Acid

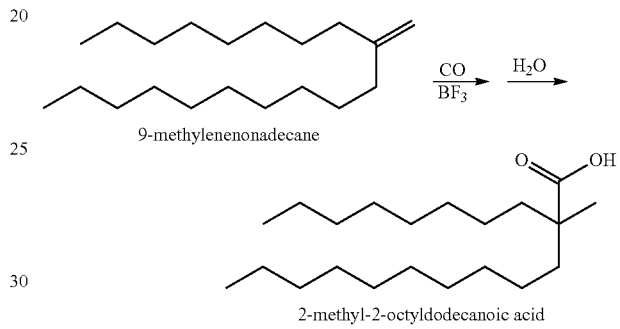

Into a 1-gallon (3.78-liter) autoclave, 1204 grams of the dimer product obtained from Example B1 above was added. Then 613 grams of $BF_3$-dihydrate was added with stirring and cooling. The reactor was then pressurized to 1000 psig with CO. Afterwards an additional 330 grams of $BF_3$ was bubbled into the reactor. The reactor was then pressurized to 2000 psig (13.79 MPa, gauge pressure) by CO and the temperature of the reactor increased to 50° C. The reaction was allowed to continue for 22 hours at the same CO pressure and the same temperature. Afterwards, the reactor was depressurized and allowed to cool to 30° C.

The reaction mixture was then pressured into a 12-liter flask containing 4 liters of water. Nitrogen gas was bubbled through the mixture for 3 hours to remove residual $BF_3$. Excess water was then drained off. The resultant mixture was then water washed seven (7) times, each time using one (1) liter of deionized water to remove the residual catalyst. Residual water in the resultant mixture was subsequently removed from with a rotary evaporator to obtain a crude product.

The total conversion of the vinylidene olefin in the carboxylation step was measured (by gas chromatography) to be 90.7%, with a yield to heavy dimer species of the vinylidene olefin measured to be 6.6%, and thus a yield to the desired neo-acid product at 84.1%.

The crude product was then batch distilled to remove lights (unreacted vinylidene olefin) and heavies to obtain a final neo-acid product. Gas chromatography of the final neo-acid product showed a concentration of neo-acid of about 98% and a concentration of heavy components of about 2%.

The final neo-acid product was measured to have a KV100 of 8.51 cSt, and a KV40 of 64.0 cSt. $^{13}$C-NMR spectra indicates that the final neo-acid product contained 2-methyl-2-octyldodecanoic acid at a purity of 98.1 wt %.

Part B: Synthesis of 2-Methyl-2-octyldodecan-1-ol

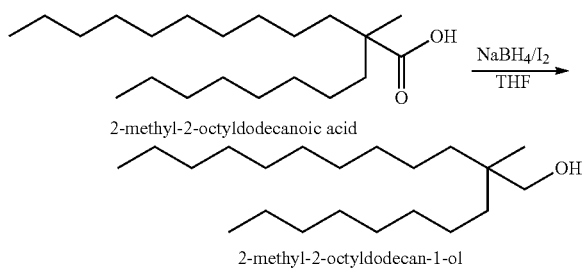

2-methyl-2-octyldodecanoic acid 2-methyl-2-octyldodecan-1-ol 7.0 g NaBH$_4$ was dissolved in anhydrous 75 ml THF in 500 ml four necked round bottom flask with stirring. Then 30 grams of 2-methyl-2-octyldodecanoic acid (MW 326.57, 0.092 mol, made pursuant to Part A of the Examples of this disclosure above) in 50 ml THF solution was added drop wise very slowly over 2 h. The mixture was stirred for 1 hour until hydrogen gas evaluation stops. A solution of iodine (18.7 grams) in 40 ml THF was added drop wise at 10 to 20° C. into a stirred mixture in about 2.5 hours, causing evolution of hydrogen, a significant exothermic and disappearance of red color of iodine. The solution was stirred overnight and heated to reflux for 1 hour. Approximately 50 ml THF was then distilled from the reaction mixture. To the cooled suspension from the residual of the distillation was added 100 ml cyclohexane and 10% NaOH solution. The solution was stirred vigorously until gas evolution ceased and the precipitated material disappeared. The mixture was then transferred into a separatory funnel. The cyclohexane solution thus separated was washed three times with 50 ml 10% NH$_3$ solution and once with 50 ml of 15% NaHS$_{O4}$ aqueous solution and once with brine solution. Evaporation of solvent gave crude 2-methyl-2-octyldodecan-1-ol. A further distillation under vacuum yielded a final purified product of 2-methyl-2-octyldodecan-1-ol of 25 grams (87%). The final purified product was confirmed by IR and NMR spectra. IR (cm$^{-1}$): 3347, 2925, 2852, 1467, 1377, 1036, 721. $^1$H NMR (CDCl$_3$): δ 3.25 (s, 2H) HO—CH$_2$—), 1.25-1.12 (m, 33H, —CH$_2$—), 0.81-0.74 (m, 9H, CH$_3$). $^{13}$C NMR (CDCl$_3$): 69.85, 37.25, 36.43, 31.95, 30.69, 29.72, 29.68, 29.38, 23.43, 22.89.4.09.

What is claimed is:

1. A compound having a formula (F-I) below:

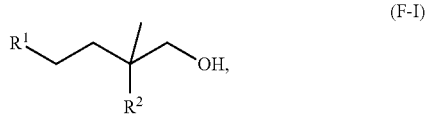

wherein R$^1$ and R$^2$ are identical and are a hydrocarbyl group comprising at least two (2) carbon atoms.

2. The compound of claim 1, wherein R$^1$ and R$^2$ are a C2 to C30 linear or branched alkyl group.

3. The compound of claim 1, wherein R$^1$ and R$^2$ are a linear alkyl group.

4. The compound of claim 2, wherein R$^1$ and R$^2$ are selected from ethyl, n-propyl, n-butyl, n-hexyl, n-octyl, n-decyl, n-dodecyl, n-tetradecyl, n-hexadecyl, n-octadecyl, n-icosyl, n-docosyl, n-tetracosyl, n-hexacosyl, and n-octacosyl.

5. The compound of claim 4, wherein R$^1$ and R$^2$ are selected from n-butyl, n-hexyl, n-octyl, n-decyl, and n-dodecyl.

6. The compound of claim 1, wherein R$^1$ and R$^2$ are a branched alkyl group.

7. The compound of claim 1, wherein R$^1$ and R$^2$ are selected from ethylhexyl, 2-propylheptanyl, 2-butyloctyl, and 3,5-dimethyloctyl.

8. A process for making a neo-alcohol product comprising a neo-alcohol compound having a formula (F-I) below:

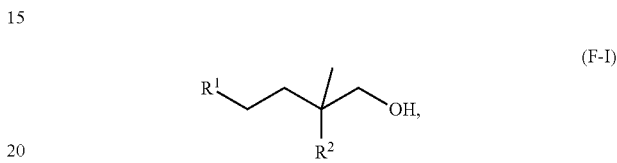

wherein R$^1$ and R$^2$ are identical and are a hydrocarbyl group comprising at least two (2) carbon atoms, the process comprising:
(I) providing a neo-acid product comprising a neo-acid compound having a formula (F-II) below:

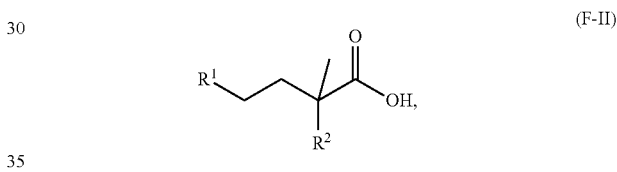

and
(II) contacting the neo-acid product with a reducing agent under reducing conditions.

9. The process of claim 8, wherein in step (II), the reducing agent is hydrogen and the reducing conditions include the presence of a hydrogenation catalyst.

10. The process of claim 9, wherein in step (II), the reducing agent is selected from: sodium borohydride (NaBH$_4$); lithium aluminum hydride; dithionate; thiosulfates; hydrazine; a mixture of NaBH$_4$ and iodine; a mixture of NaBH$_4$ and H$_2$SO$_4$; a mixture of NaBH$_4$, catechol, and CF$_3$COOH; a mixture of NaBH$_4$ and ZnC$_{12}$; and a mixture of NaBH$_4$ and cyanuric chloride.

11. The process of claim 10, wherein the reducing conditions include a temperature in the range from 10 to 60° C., and a reaction time in the range from 0.5 to 24 hours.

12. The process of claim 8, wherein R$^1$ and R$^2$ are a C2 to C30 linear alkyl groups.

13. The process of claim 8, wherein R$^1$ and R$^2$ are selected from ethyl, n-propyl, n-butyl, n-hexyl, n-octyl, n-decyl, n-dodecyl, n-tetradecyl, n-hexadecyl, n-octadecyl, n-icosyl, n-docosyl, n-tetracosyl, n-hexacosyl, and n-octacosyl.

14. The process of claim 13, wherein R$^1$ and R$^2$ are selected from n-butyl, n-hexyl, n-octyl, n-decyl, and n-dodecyl.

15. The process of claim 8, wherein R$^1$ and R$^2$ are a linear alkyl group.

16. The process of claim 8, wherein step (I) comprises:
(Ia) providing a vinylidene olefin feed comprising a vinylidene olefin having the following formula (F-III):

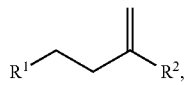 (F-III)

where $R^1$ and $R^2$ correspond to the $R^1$ and $R^2$ in formula (F-I);

(Ib) contacting the vinylidene olefin with carbon monoxide in a reactor in the presence of an acid catalyst at a carbon monoxide partial pressure of at least 1.0 MPa to obtain a reaction mixture;

(Ic) contacting the reaction mixture with water to obtain an acid product mixture; and (Id) obtaining at least a portion of the neo-acid product from the acid product mixture.

17. The process of claim 16, wherein step (Ia) comprises the following steps:

(Ia.1) providing a monomer feed comprising a terminal olefin where $R^1$ and $R^2$ correspond to the $R^1$ and $R^2$ in formula (F-I);

(Ia.2) oligomerizing the monomer feed in an oligomerization reactor in the presence of a catalyst system comprising a metallocene compound to obtain an oligomerization product mixture; and (Ia.3) obtaining at least a portion of the vinylidene olefin feed from the oligomerization product mixture.

18. The process of claim 17, wherein step (Ia.2) is carried out in a continuous process.

19. The process of claim 8, wherein in step (I), the neo-acid compound is selected from: 2-ethyl-2-methylhexanoic acid; 2-methyl-2-propylheptanoic acid; 2-butyl-2-methyloctanoic acid; 2-methyl-2-pentylnonanoic acid; 2-hexyl-2-methyldecanoic acid; 2-heptyl-2-methylundecanoic acid; 2-methyl-2-octyldodecanoic acid; 2-decyl-2-methyltetradecanoic acid; 2-dodecyl-2-methylhexadecanoic acid; 2-methyl-2-tetradecyloctadecanoic acid; and 2-methyl-2-hexadecylicosanoic acid.

* * * * *